United States Patent [19]

Hull et al.

[11] Patent Number: 5,269,810
[45] Date of Patent: Dec. 14, 1993

[54] PATCH ELECTRODE

[75] Inventors: John R. Hull, Flagstaff, Ariz.; Craig D. Lack, Newark, Del.; William P. Mortimer, Jr., Conowingo, Md.; Richard A. Staley, Flagstaff, Ariz.

[73] Assignee: W. L. Gore & Associates, Inc., Newark, Del.

[21] Appl. No.: 901,317

[22] Filed: Jun. 19, 1992

[51] Int. Cl.⁵ ............................................. A61N 1/04
[52] U.S. Cl. .................................... 607/129; 128/639; 128/642
[58] Field of Search ............... 128/639, 640, 641, 642, 128/419 D, 784, 798, 802

[56] References Cited

U.S. PATENT DOCUMENTS

| | | | |
|---|---|---|---|
| 3,474,775 | 10/1969 | Johnson | 128/639 |
| 3,953,566 | 4/1976 | Gore . | |
| 4,030,509 | 6/1977 | Heilman et al. . | |
| 4,166,453 | 9/1979 | McClelland | 128/639 |
| 4,291,707 | 9/1981 | Heilman | 128/784 |
| 4,499,907 | 2/1985 | Kallok et al. . | |
| 4,542,752 | 9/1985 | DeHaan | 128/784 |
| 4,573,480 | 3/1986 | Hirschberg . | |
| 4,576,174 | 3/1986 | Miyazaki et al. . | |
| 4,641,656 | 2/1987 | Smits . | |
| 4,662,377 | 5/1987 | Heilman et al. . | |
| 4,690,155 | 9/1987 | Hess . | |
| 4,765,341 | 8/1988 | Mower | 128/785 |
| 4,827,932 | 5/1989 | Idekar et al. . | |
| 4,955,381 | 9/1990 | Way et al. | 128/640 |
| 4,972,846 | 11/1990 | Owens | 128/784 |
| 4,998,536 | 3/1991 | Scharnberg | 128/798 X |
| 5,076,286 | 12/1991 | Scharnberg | 128/798 X |
| 5,087,242 | 2/1992 | Petelenz et al. | 604/20 |
| 5,148,566 | 9/1992 | Fukui et al. | 128/639 |

FOREIGN PATENT DOCUMENTS

| | | | |
|---|---|---|---|
| 0000759 | 2/1979 | European Pat. Off. | 128/802 |
| 0263586 | 4/1988 | European Pat. Off. . | |
| 0269200 | 6/1988 | European Pat. Off. . | |
| 0360496 | 3/1990 | European Pat. Off. . | |
| 0375440 | 6/1990 | European Pat. Off. | 128/639 |
| 2182566 | 11/1989 | United Kingdom . | |
| 9014860 | 12/1990 | World Int. Prop. O. . | |

OTHER PUBLICATIONS

D. Santel et al., Implantable Defibrillator Electrode System: A Brief Review PACE vol. 8, Jan.-Feb. 1985, pp. 123-131.

Primary Examiner—Kyle L. Howell
Assistant Examiner—Jeffrey R. Jastrzab
Attorney, Agent, or Firm—Wayne D. House

[57] ABSTRACT

A flexible patch electrode for use with living tissue, comprising, in sequential laminar form, a layer of electrically conductive porous polytetrafluoroethylene, a layer of polymeric adhesive, a layer of electrically conductive sheet material having lower resistivity than the layer of porous polytetrafluoroethylene, and an insulating layer. The layer of electrically conductive sheet material is of less length and width than the adjacent layers and is placed so that its edges are not exposed at the edges of the flexible patch electrode.

19 Claims, 1 Drawing Sheet

PATCH ELECTRODE

FIELD OF THE INVENTION

This invention relates to the field of patch electrodes for use with defibrillators.

BACKGROUND OF THE INVENTION

Cardiac arrhythmias such as tachyrhythmia frequently result in ventricular fibrillation which in turn often results in death. Ventricular fibrillation is effectively treated by defibrillation, the non-synchronized delivery of electrical energy to the heart which stops the ventricular fibrillator and allows the heart to resume a normal rhythm.

The electrical energy is commonly delivered to the heart by two methods. Transvenous cardioversion leads are introduced to the heart through a catheter inserted through the venous system. This method is most appropriate to allow defibrillation when it is anticipated that defibrillation may only be required for a temporary period. It has the advantage that the energy source necessary to provide the electrical stimulus may remain outside the body.

The second method involves the use of patch electrodes that are permanently implanted on the surface of the heart. The energy source is permanently implanted as well. The disadvantages of the second method are that complex surgery is required and that the energy source is bulky, causing a substantial protrusion from below the surface of the skin. This method allows for immediate defibrillation any time the implanted system senses a ventricular defibrillation. It has been demonstrated to be an effective solution that has been widely employed for many years. It is intended to be a permanent solution, requiring only that batteries in the implanted energy source be replaced at relatively long intervals such as about three years. Finally, this method is entirely portable, allowing full mobility of the patient having such an implanted system. It is commonly believed that the benefits of the implanted systems far outweigh their disadvantages.

The implanted patch electrodes that transmit the electrical energy to the surface of the heart have various functional requirements that are difficult to achieve. These include biocompatibility, flexibility, effective attachment methods and the necessity to distribute the electrical charge so that it may be effectively delivered without burning or otherwise damaging the tissue to which it is attached.

Many various patch electrode designs have been proposed. U.S. Pat. No. 4,291,707 discloses a defibrillator electrode comprising a tissue contacting layer of electrically conductive wire mesh, the mesh having a backing layer of silicone rubber. The silicone rubber also encloses the periphery of the wire mesh. The backing layer of silicone rubber may optionally incorporate a reinforcing layer of Dacron ® fabric.

U.S. Pat. No. 4,542,752 describes an implantable electrode tip assembly wherein the conductive surface comprises a layer of porous carbon deposited by glow discharge plasma onto the outer surface of a porous, electrically conductive substrate such as porous titanium.

U.S. Pat. 4,972,846 teaches the construction of a patch electrode comprising an insulating layer of porous expanded PTFE laminarly bonded to an electrically conductive layer of metal plated porous expanded PTFE.

U.S. Pat. No. 5,087,242 describes a hydratable skin-contact bioelectrode comprising a layer of conductive, hydratable material, a layer of conductive sheet material, and a support base on which the other layers are mounted. The layer of conductive, hydratable material is capable of absorbing solutions but not capable of discharging the absorbed solution by mechanical means such as squeezing in the fashion of sponges or other fibrous masses. The conductive, hydratable material may be a fibrous polymer or other type of matrix material impregnated with a hydratable polymer, or a layer of granulated polymer between two layers of hydrophilic material. Materials described as useful for the conductive electrode surface include polyethylene oxide, polyacrylamide and ammonium polyacrylate.

Patent GB 2,182,566 A relates a patch defibrillator electrode comprising a layer of electrically conductive metal foil having a pattern of slits through the entire thickness of the foil to provide the foil with good flexibility. The foil layer has an optional insulating backing of a porous insulating material such as Dacron fabric. The porous insulating material may also be used to enclose the peripheral edges of the foil. The porous insulating material may optionally incorporate a biologically active agent for inhibiting thrombus formation.

U.S. patent application Ser. No. 07/456,113, now U.S. Pat. No. 5,148,806, teaches the construction of an electrode for use on a living body, t electrode comprising porous polytetrafluoroethylene containing a conductive powder, preferably either carbon black or metal.

SUMMARY OF THE INVENTION

The present invention is a flexible patch electrode comprising, in sequential laminar relationship, an electrically conductive layer of porous PTFE, a layer of polymeric adhesive, a layer of electrically conductive sheet material of lower resistivity than the electrically conductive porous PTFE layer, and a layer of electrically insulating material. The electrically conductive sheet material should be of resistivity at least about two orders of magnitude less than the resistivity of the electrically conductive layer of porous PTFE. The layer of polymeric adhesive is preferably made to be electrically conductive by the addition of an electrically conductive material such as carbon black. The electrically conductive sheet material should be of less width and length than the electrically conductive layer of porous PTFE and the layer of electrically insulating material, and should be centered within the respective areas of those layers so that the electrically conductive sheet material is not exposed at the edges of the patch electrode.

The patch electrode of the present invention is intended for use primarily as an implantable defibrillator electrode. It may be used with conventional energy sources and conventional implantable lead wires.

DETAILED DESCRIPTION OF THE INVENTION

Figure 1:
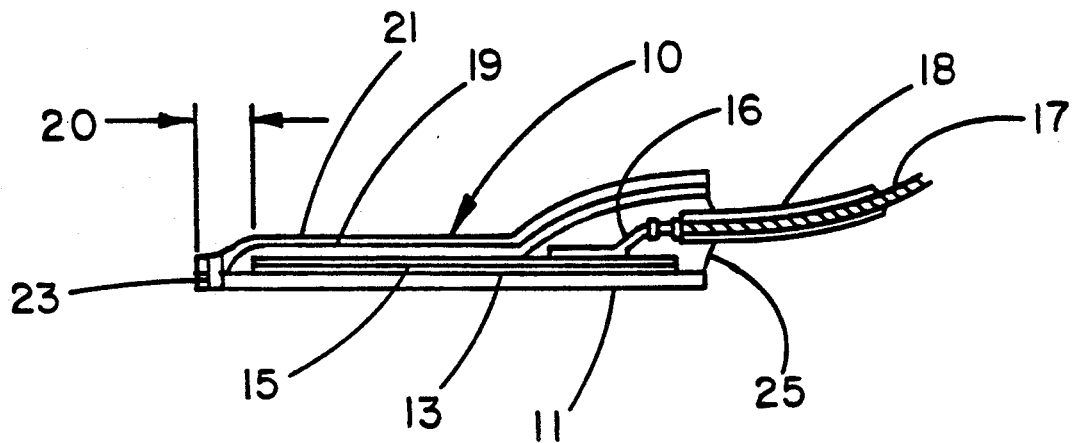
FIG. 1 describes a cross section of the flexible patch electrode of the present invention.
Figure 2:
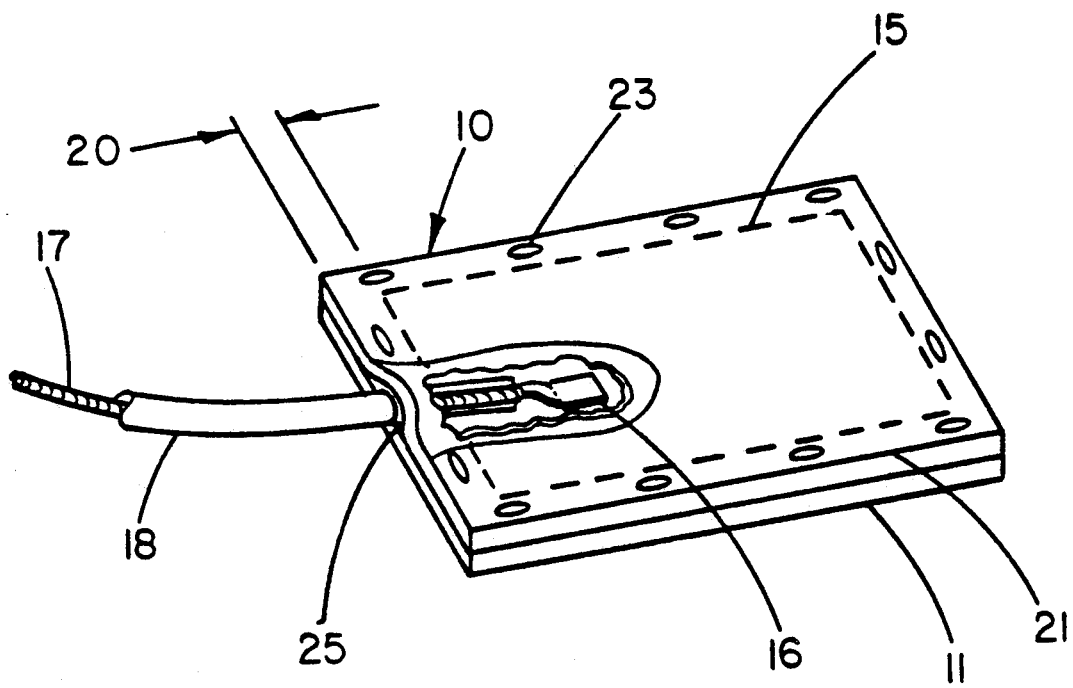
FIG. 2 describes a perspective view of the electrode.

FIG. 1 describes a cross section of the flexible patch electrode 10 of the present invention; FIG. 2 describes a perspective view of the electrode. The construction of the patch electrode 10 comprises, in sequential laminar form, a layer of electrically conductive porous PTFE 11 which is conductively adhered by a layer of polymeric adhesive 13 to a layer of electrically conductive sheet material 15. An implantable lead wire 17 is connected to the surface of the electrically conductive sheet material 15 that is opposite the layer of electrically conductive porous PTFE 11. The surface of the electrically conductive sheet material 15 with the connected implantable lead wire 17 is covered by a layer of electrically insulating material 21 that is optionally adhered by a layer of adhesive 19.

Adhesive layers 13 and 19 are not shown in the perspective view of FIG. 2 because in the finished electrode these layers are typically very thin.

The flexible patch electrode 10 is intended to function by the laminar combination of the electrically conductive sheet material 15 and the layer of electrically conductive porous PTFE 11 that is of greater resistivity than the layer of electrically conductive sheet material 15. The layer of electrically conductive sheet material 15 first receives an electrical charge via the connected implantable lead wire 17 from a remote defibrillator energy source. The charge is quickly dispersed throughout layer 15 because of its relatively low resistivity. The charge is then uniformly applied to the heart surface through the layer of electrically conductive porous PTFE 11 because of the greater resistivity of this layer in comparison to that of the layer of electrically conductive sheet material 15.

Porous PTFE is the preferred material for both the conductive electrode surface layer 11 and for the reverse layer of electrically insulating material 21 because it is both highly biocompatible and highly flexible with a long flex life. Porous PTFE has a long history of use as an implantable biomaterial with over one million implants in the form of products including vascular grafts, hernia repair patches, ligaments, sutures and periodontal repair materials. The preferred porous PTFE is porous expanded PTFE having a microstructure of nodes interconnected by fibrils, made according to the teachings of U.S. Pat. Nos. 3,953,566 and 4,187,390.

The porous PTFE comprising the conductive electrode surface layer 11 is made to be electrically conductive by incorporation with an electrically conductive filler which is preferably carbon black. The term carbon black as used herein includes various forms of conductive carbon including carbon black, acetylene black, channel black, gas black, furnace black, and various forms of graphite. Acetylene black is typically the most electrically conductive of these and therefore may be preferred for some applications. Other electrically conductive fillers may also be used, including fibers, particulates or flakes of carbon black, and metal particulates, flakes or fibers such as gold, platinum, titanium, stainless steel and silver. Some metal oxide particulates may also be used. It is important that the biocompatibility of the filler material be appropriate for the intended application of the electrode. For use as an implantable defibrillator electrode, it is believed that the most appropriate fillers are carbon blacks, platinum, titanium and stainless steel. The conductive filler materials should be substantially uniformly distributed throughout the volume of the layer of porous PTFE in which they are contained.

The preferred material for the electrically conductive porous PTFE layer 11 is porous, expanded, conductive PTFE commercially available from W. L. Gore and Associates, Cherry Hill, Md. (part no. 5748419). The Gore material used to construct examples of present invention is about 0.13 mm thick, is of about 10 micron fibril length, has a density of about 0.4 g/cc, contains about 25% carbon black by weight and has a volume resistivity of about 94 ohm-cm. Volume resistivity was measured by the method taught by U.S. Military Specification MIL-G-83528A, pressure probe method with the probe pressure reduced to about 1.4 kg/cm$^2$ (20 lb/in$^2$) in order to avoid undue crushing of the porous electrode material. Fibril length is measured as taught by U.S. Pat. No. 4,972,846.

Alternatively, the conductive PTFE layer may be manufactured by uniformly distributing an electrically conductive filler throughout the porous PTFE during the process of making the PTFE layer. For example, if porous expanded PTFE is used, the electrically conductive particulate may be blended with the powdered PTFE resin prior to extrusion and expansion. The manufacture of porous expanded PTFE filled with various materials such as electrically conductive particulates is described in U.S. Pat. Nos. 3,953,566; 4,096,227; 4,187,390; and U.S. patent application Ser. No. 07/456,113.

The layer of electrically conductive sheet material 15 is preferably a flexible metal foil such as platinum of about 0.008 mm thickness. Other metal foils such as titanium are also believed to be satisfactory. The use of the term metal herein includes metals in both elemental and alloy forms. The foils must be thin enough to provide for good flexibility and flex life characteristics and must be of adequate biocompatibility. Still other conductive sheet materials may be used such as woven metallic fabrics, wire screens or intrinsically conductive polymers.

The conductive sheet material 15 is conductively adhered to the electrically conductive porous PTFE layer 12 with a polymeric adhesive 13. Preferably, the polymeric adhesive is a thermopolymer and more preferably a fluoropolymer. Most preferably the adhesive is an electrically conductive adhesive, however, it has surprisingly been found that a thin layer of non-conductive polymeric adhesive produces good adhesion with little additional electrical resistance. One such non-conductive adhesive is a dispersion of water, fluorinated ethylene propylene (hereinafter FEP) in the form of a particulate, and a surfactant, available from DuPont (Wilmington, Del.) under the product name Teflon ® FEP 120 Aqueous Dispersion. Alternatively, conductive fillers such as carbon black may be added to this dispersion in order to make it electrically conductive. Six percent acetylene black (Shawinigan Acetylene Black, Gulf Canada Ltd., Montreal, Quebec, Canada) by weight of FEP has been found adequate to provide the adhesive with suitable electrical conductivity. This dispersion with and without acetylene black has been found useful in the construction of the patch electrode of the present invention.

The lead wire 17 necessary to conduct the electrical charge from the source of electrical energy to the patch electrode 10 must be connected to the conductive sheet material 15. If the conductive sheet material 15 is a metal foil or wire mesh, then the lead wire 17 is preferably connected by welding and most preferably by resistance welding. An alternative connection method involves connecting the end of the lead wire 17 to a connecting tab 16 by welding or crimping or both; the flat surface of connecting tab 16 is then welded to the surface of the foil or mesh 15 Conventional implantable lead wires 17 such as helically wound wires having an outer insulating sleeve 18 of silicone may be used with the inventive electrode. A strain relief 25 should be used at the point of connection of the lead wire 17 to the conductive sheet material 15 to reduce the risk of connection failure.

The electrically insulating layer 21 of the inventive electrode 10 that is the layer 21 comprising the reverse side of the electrode 10 opposite the conductive electrode surface 11 is required to be highly flexible and biocompatible for cardiac defibrillation applications. While non-porous materials may be used, the preferred material for the electrically insulating layer 21 is porous expanded PTFE of relatively short fibril length such as about 1 micron in order to resist tissue ingrowth into the void space of the porous material. The porosity is desirable to maximize flexibility of the insulating layer. The insulating layer 21 is adhered to the side of the conductive sheet material 15 opposite the conductive electrode layer 11. The means for adherance is preferably a layer 19 of flexible adhesive such as silicone adhesive, for example, Rehau Raumedic SI1511, Germany. The use of such an adhesive that closes off and seals the adhesive-coated porous surface of the insulating layer is required. If a porous insulating material is used without a sealant such as a silicone adhesive, the porous insulating material can be expected to wet out with body fluids with a resultant loss of electrical insulating capability.

Alternatively, if a non-porous thermoplastic material is used for the electrically insulating layer 21. It may be thermally bonded to the layer of electrically conductive sheet material 15 without the use of adhesive layer 19. An example of such a non-porous thermoplastic insulating material is FEP sheet material. Another alternative nonporous insulating material is the use of a silicone adhesive alone applied over the surface of the electrically conductive sheet material opposite the electrically conductive porous PTFE.

The process of making the inventive electrode 10 begins with attaching one end of a length of lead wire 17 to one surface of the sheet of electrically conductive material 15. A 51 mm × 51 mm sheet of platinum foil of 0.008 mm thickness was used to make all test examples of the inventive electrode 10. A lead wire 17 was attached to one surface of the sheet of platinum foil by first crimp connecting the end of the lead wire 17 to a spatula-shaped connecting tab 16. The surface of the connecting tab 16 was then connected to the surface of the platinum foil 15 by resistance welding at about the center of the width of that surface as shown by FIGS. 1 and 2.

It was found that bonding of the platinum foil 15 to the conductive layer of porous PTFE 11 was enhanced by first etching the platinum foil 15 in an etching solution such as aqua regia for about 30 minutes at room temperature. The aqua regia used was comprised of 1 part 70% $HNO_3$ and 3 parts of 37% HCl. After etching of the foil 15. four coats of DuPont Teflon FEP 120 Dispersion were applied to the platinum foil 15 on the side opposite the lead wire 17. Each coat was force dried by the application of hot air before applying the subsequent coat. Likewise, four coats of the same FEP dispersion except with the addition of 6% acetylene black as previously described were applied to one side of a sheet of conductive porous expanded PTFE 11. This conductive porous expanded PTFE was the same material described previously as available from W. L. Gore & Associates, Inc., Cherry Hill, Md.

The FEP coatings on the platinum foil and the conductive porous expanded PTFE were melted to create a coherent coating with a smooth surface and uniform thickness. Any heat source that accomplishes this purpose without damaging the substrate material may be used. In the present case this was accomplished by exposing the FEP coating on the platinum foil to heat from a 350 watt infrared lamp for 30 seconds, and by exposing the FEP coating on the conductive porous expanded PTFE to hot air from a hot air gun at about 300–325° C. After being allowed to cool at room temperature, the FEP coated surface of the 51 mm × 51 mm sheet of platinum foil 15 was centrally placed onto the FEP coated surface of the 56 mm × 56 mm sheet of conductive porous expanded PTFE 11 so that a 2.5 mm wide margin 20 of the sheet of conductive porous expanded PTFE 11 was exposed around the edges of the sheet of platinum foil 15. A metal iron having a smooth surface heated to between 300 and 325° C. was then applied onto the exposed surface of the platinum foil 15 with slight pressure until the FEP coating had melted. After the resulting laminate was allowed to cool, it was found that the platinum foil 15 was securely bonded to the sheet of conductive, porous expanded PTFE 11.

The exposed surface of the platinum foil 15 was then treated with a silicone adhesive primer (McGhan NuSil, Carpinteria, Calif., part no. CF2-135) and cured for one-half hour in a humidity chamber at about 40° C. and 100% relative humidity.

The lead wire attachment was provided with a strain relief in the form of silicone boot 25 molded from medical grade silicone (Dow Corning Silastic Q7-4865, Midland, Mich.). The boot 25 was slipped over the insulation 18 of the lead wire 17 after attachment of the lead wire 17 to the electrically conductive sheet 15. The silicone boot 25 was adhered to the lead wire insulation 18 and to the surface of the electrically conductive sheet 15 with medical grade silicone adhesive.

For use as the electrically insulating layer 21, a 56 mm × 56 mm sheet of 0.1 mm thick GORE-TEX® Expanded PTFE Surgical Membrane (W. L. Gore & Associates, Inc., Flagstaff, Ariz.) was provided with a coat of the medical grade silicone adhesive on one surface. The adhesive coated surface was then firmly placed onto the exposed surface of the platinum foil 15 so that the edges of the sheet of surgical membrane were even with the edges of the sheet of conductive porous expanded PTFE 11. The silicone adhesive was then cured for 2 hours in a humidity chamber at 40° C. and 100% relative humidity.

The 2.5 mm margin 20 can be provided with suture holes 23 at intervals to enable attachment of the patch electrode to a heart surface by suturing.

Two defibrillator patches made according to the above description were sutured onto opposing surfaces of the heart of a 31 kg greyhound dog. After inducing fibrillation, 30 joules were applied through the lead wires of the two patches from a Hewlett Packard model 43110A defibrillator/monitor. Immediate defibrillation was obtained.

To test the conductivity of different polymeric adhesives, three additional laminations of platinum foil and electrically conductive porous PTFE were made using different combinations of adhesives to bond the two layers. Each of these additional examples was made using a sheet of 20.4 mm×20.4 mm, 0.008 mm thick platinum foil that was adhered to the center of the surface of a 25.4×25.4 mm sheet of electrically conductive porous PTFE of the type previously described. None of these three examples incorporated a lead wire 17 or the electrically insulating layer 21. The first example, Sample A, was made as described previously with four coats of the FEP dispersion without acetylene black applied to one side of the platinum foil and four coats of the FEP dispersion incorporating acetylene black applied to one surface of the electrically conductive porous PTFE. The second example, Sample B, was made by the application of four coats of the FEP dispersion applied to one surface of the platinum foil and four coats of the FEP dispersion to one surface of the electrically conductive porous PTFE; no conductive filler was used with the dispersion applied to Sample B. The third example, Sample C, incorporated a sheet of 25.4 mm×25.4 mm, 0.013 mm thick FEP film placed between the platinum foil and the electrically conductive porous PTFE. For this example, four coats of the FEP dispersion without conductive filler were applied to one surface of the platinum foil, but no dispersion was used on the electrically conductive porous PTFE. For each example, an iron having a smooth surface heated to about 300–325° C. was applied to the exposed surface of the platinum foil with firm hand pressure for about 60 seconds, causing the FEP adhesive to melt. After being allowed to cool to ambient temperature, the foil was found to be well adhered to the electrically conductive porous PTFE for each example. A volume resistivity measurement was made of each of the three examples; using an electrode area of 1.61 cm$^2$ and a laminate thickness of 0.13 mm, the resistance of each sample was measured as described previously and volume resistivity was calculated as the product of resistance and electrode area, divided by sample thickness. The results are described in Table 1. Samples A and B were believed to have electrical characteristics suitable for an effective defibrillator patch electrode; Sample C had excessive resistance for use as a defibrillator patch electrode.

TABLE 1

|  | Sample A | Sample B | Sample C |
|---|---|---|---|
| Resistance, ohms | .24 | 1.3 | 30 |
| Volume Resistivity, ohm-cm | 77 | 430 | 9800 |

We claim:
1. A flexible patch electrode for use with living tissue, comprising, in sequential laminate form,
   a) a layer of electrically conductive porous polytetrafluoroethylene; and
   b) a layer of polymeric adhesive, and
   c) a layer of electrically conductive sheet material of lower resistivity than the layer of electrically conductive porous polytetrafluoroethylene; and
   d) a layer of electrically insulating material;
wherein the layer of electrically conductive sheet material is of less length and width than the layer of electrically conductive porous polytetrafluoroethylene and the layer of electrically insulating material, the layer of electrically conductive sheet material being placed within the patch electrode so that the edges of the layer of electrically conductive sheet material are not exposed at the edges of the patch electrode.

2. A flexible patch electrode according to claim 1 wherein the layer of electrically conductive sheet material is of at least two orders of magnitude lower resistivity than the resistivity of the layer of electrically conductive porous polytetrafluoroethylene.

3. A flexible patch electrode according to claim 1 wherein the layer of electrically conductive porous polytetrafluoroethylene is electrically conductive porous expanded polytetrafluoroethylene.

4. A flexible patch electrode according to claim 1 wherein the electrically conductive porous polytetrafluoroethylene contains an electrically conductive filler.

5. A flexible patch electrode according to claim 4 wherein the electrically conductive filler is chosen from the group consisting of carbon blacks, platinum, gold, silver, titanium and stainless steel.

6. A flexible patch electrode according to claim 1 wherein the layer of polymeric adhesive is a thermoplastic.

7. A flexible patch electrode according to claim 6 wherein the thermoplastic is a fluoropolymer.

8. A flexible patch electrode according to claim 7 wherein the fluoropolymer is fluorinated ethylene propylene.

9. A flexible patch electrode according to claim 8 wherein the polymeric adhesive is a conductive polymeric adhesive comprising a mixture of carbon black and the fluorinated ethylene propylene.

10. A flexible patch electrode according to claim 9 wherein the carbon black is acetylene black.

11. A flexible patch electrode according to claim 1 wherein the layer of electrically conductive sheet material is metallic.

12. A flexible patch electrode according to claim 11 wherein the layer of electrically conductive sheet material is a metal foil.

13. A flexible patch electrode according to claim 12 wherein the metal foil is substantially platinum.

14. A flexible patch electrode according to claim 12 wherein the metal foil is substantially gold.

15. A flexible patch electrode according to claim 12 wherein the metal foil is substantially titanium.

16. A flexible patch electrode according to claim 12 wherein the metal foil is substantially stainless steel.

17. A flexible patch electrode according to claim 11 wherein the layer of electrically conductive sheet material is a woven wire mesh.

18. A flexible patch electrode according to claim 1 wherein the layer of electrically insulating material is porous polytetrafluoroethylene which is adhered to the layer of electrically conductive sheet material with an adhesive that seals the porous surface of the layer of electrically insulating material to which it is applied.

19. A flexible patch electrode according to claim 1 wherein:
   a) the layer of electrically conductive porous polytetrafluoroethylene is porous expanded polytetrafluoroethylene containing a filler of carbon black; and
   b) the layer of polymeric adhesive is a mixture of fluorinated ethylene propylene and an electrically conductive filler; and
   c) the layer of electrically conductive sheet material is platinum foil; and
   d) the layer of electrically insulating material is porous expanded polytetrafluoroethylene adhered to the platinum foil by a silicone adhesive.

* * * * *